United States Patent
Lee et al.

(10) Patent No.: US 10,285,895 B2
(45) Date of Patent: May 14, 2019

(54) METHOD FOR SETTING MASSAGE PATTERN OF THERMOTHERAPY DEVICE

(71) Applicant: Ceragem Co., Ltd., Cheonan-si, Chungcheongnam-do (KR)

(72) Inventors: Taek Seung Lee, Chungcheongnam-do (KR); Sang Ui Choi, Seoul (KR); Chang Soo Park, Seongnam-si (KR); Yong Hee Kim, Chungcheongbuk-do (KR); Hea Sung Lee, Chungcheongnam-do (KR)

(73) Assignee: CERAGEM CO., LTD. (KR)

( * ) Notice: Subject to any disclaimer, the term of this patent is extended or adjusted under 35 U.S.C. 154(b) by 383 days.

(21) Appl. No.: 14/354,074

(22) PCT Filed: Oct. 24, 2012

(86) PCT No.: PCT/KR2012/008784
§ 371 (c)(1),
(2) Date: Apr. 24, 2014

(87) PCT Pub. No.: WO2013/062321
PCT Pub. Date: May 2, 2013

(65) Prior Publication Data
US 2014/0371638 A1    Dec. 18, 2014

(30) Foreign Application Priority Data

Oct. 24, 2011 (KR) .................. 10-2011-0109022
Oct. 24, 2011 (KR) .................. 10-2011-0109023
(Continued)

(51) Int. Cl.
| | | |
|---|---|---|
| A61F 7/00 | (2006.01) |
| A61H 39/06 | (2006.01) |
| A61H 7/00 | (2006.01) |
| A61F 7/03 | (2006.01) |
| A61H 15/00 | (2006.01) |

(52) U.S. Cl.
CPC .............. A61H 7/00 (2013.01); A61F 7/007 (2013.01); A61F 7/034 (2013.01);
(Continued)

(58) Field of Classification Search
CPC ........ A61H 2230/825; A61H 2230/855; A61H 7/007; A61H 2007/009; A61H 15/00;
(Continued)

(56) References Cited

U.S. PATENT DOCUMENTS

| | | | | |
|---|---|---|---|---|
| 4,173,972 A | * | 11/1979 | Kodera ................. | A61H 7/004 601/102 |
| 4,421,110 A | * | 12/1983 | DeLisle ................ | A61H 7/001 601/134 |

(Continued)

FOREIGN PATENT DOCUMENTS

| | | |
|---|---|---|
| CN | 201453636 | 5/2010 |
| CN | 101947175 | 1/2011 |

(Continued)

Primary Examiner — Michael J Tsai
(74) Attorney, Agent, or Firm — Riverside Law LLP

(57) ABSTRACT

The present invention relates to a method for setting a massage pattern of a thermotherapy device, and more specifically, to a method for setting a massage pattern, wherein the movement of a moxibustion device is patterned according to diseases so as to allow a bone of the spine associated with a disease to be intensively massaged, and thus if a disease is selected, a moxibustion device is operated by a motor according to the set massage pattern so as to enable an automatic customized massage according to the disease.

18 Claims, 14 Drawing Sheets

(30) Foreign Application Priority Data

Oct. 24, 2011 (KR) ........................ 10-2011-0109024
Oct. 24, 2011 (KR) ........................ 10-2011-0109025

(52) U.S. Cl.
CPC ......... *A61H 15/0078* (2013.01); *A61H 39/06* (2013.01); *A61F 2007/0071* (2013.01); *A61F 2007/0088* (2013.01); *A61H 2015/0028* (2013.01); *A61H 2201/0207* (2013.01); *A61H 2201/0221* (2013.01); *A61H 2201/0228* (2013.01); *A61H 2201/0257* (2013.01); *A61H 2201/1623* (2013.01); *A61H 2201/1654* (2013.01); *A61H 2201/1669* (2013.01); *A61H 2201/5064* (2013.01); *A61H 2203/0456* (2013.01); *A61H 2205/081* (2013.01); *A61H 2230/855* (2013.01); *F04C 2270/041* (2013.01)

(58) Field of Classification Search
CPC .... A61H 15/0078; A61H 15/02; A61H 39/00; A61H 39/007; A61H 39/02; A61H 39/04; A61H 39/06; A61H 2201/0138; A61H 2201/0142; A61H 2201/0146; A61H 2201/5002; A61H 2205/081; A61B 5/00
USPC .................................................. 600/584, 587
See application file for complete search history.

(56) References Cited

U.S. PATENT DOCUMENTS

| | | | |
|---|---|---|---|
| 4,699,126 A * | 10/1987 | Lancaster | A61H 1/00 601/102 |
| 6,258,047 B1 * | 7/2001 | Muramatsu | A61B 5/103 600/594 |
| 6,606,520 B1 * | 8/2003 | Lee | A61F 7/00 601/19 |
| 7,410,493 B1 * | 8/2008 | Chen | A61H 39/00 606/204 |
| 7,517,327 B1 * | 4/2009 | Knight | A61H 7/00 601/134 |
| 2004/0158176 A1 * | 8/2004 | Park | A61H 15/0078 601/18 |
| 2004/0243030 A1 * | 12/2004 | Tanizawa | A61H 7/00 601/90 |
| 2004/0260215 A1 * | 12/2004 | Kim | A61H 15/0078 601/99 |
| 2008/0269629 A1 * | 10/2008 | Reiner | A61B 5/4836 600/544 |

FOREIGN PATENT DOCUMENTS

| | | |
|---|---|---|
| JP | 2000-334011 | 12/2000 |
| JP | 2001-029418 | 2/2001 |
| JP | 2005-137759 A | 6/2005 |
| JP | 2007-014458 | 1/2007 |
| JP | 2011-505963 | 3/2011 |
| KR | 200243024 Y1 | 8/2001 |
| KR | 20-0275399 Y1 | 5/2002 |
| KR | 10-2002-0087720 | 11/2002 |
| KR | 10-2003-0063775 | 7/2003 |
| KR | 10-2003-0069647 | 8/2003 |
| KR | 100422111 B1 | 2/2004 |
| KR | 10-2004-0101947 | 12/2004 |
| WO | WO 02/069880 | 9/2002 |

* cited by examiner

FIG. 4

| Disease | Related organ | Vertebrae |
|---|---|---|
| Dyspepsia | Spleen, stomach, liver, gall bladder, small intestine | T9-T12,S1 |
| Blood circulation | Heart, small intestine, kidney, lungs, spleen, liver, adrenal gland, stomach | C3-C6,T1-T12 |
| Immune boosting | Spleen, metacarpus, tonsil, liver, circulation of lymph | C6,T5-T9,T12 |
| Sexual dysfunction | Spleen, kidney, bladder, lungs | T3,T11,L2,S2 |
| Attention deficit disorder | Head, eyes, nose, lungs, pancreas, liver, adrenal gland, diaphragmatic pleura | C1-C4,T1-T10 |
| Insomnia | Kidney, liver, heart | T5,T9,L2 |
| Obesity | Spleen, kidney, small intestine | T4-T12,L2,S1 |
| Cervical vertebrae pain | Neck muscles, Fengchi points, Tianzhu points | C3,C4,C7-T1 |
| Lumbar disc | Peripheral lumbosacral muscles | L1-L5,S1,S2 |

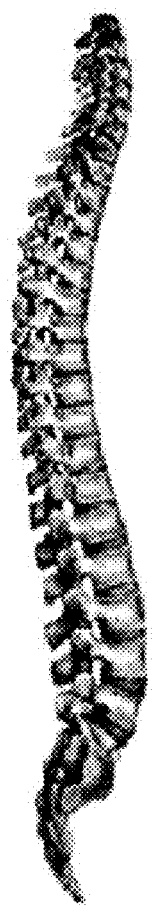
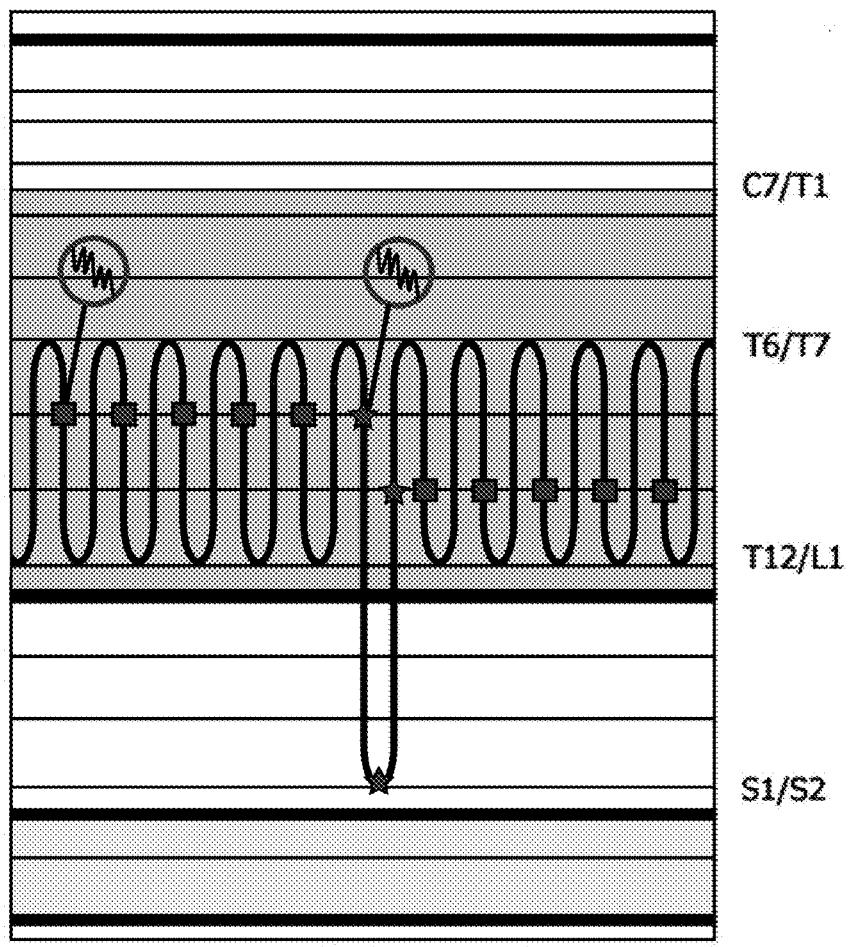
FIG. 5A

| Disease | Sympathetic nerve | Parasympathetic nerve |
|---|---|---|
| Blood circulation | ◯ | ◯ |
| Immune boosting |  | ◯ |
| Insomnia |  | ◯ |
| Obesity | ◯ |  |

FIG. 12

| Disease | Related organ | Vertebrae |
|---|---|---|
| Dyspepsia | T8/T9,T10/T11,S1/S2 | T8/T9,T10/T11,S1/S2 |
| Blood circulation | T2/T3,T4/T5,T6/T7,T8/T9, T10/T11,T12/L1 | T2/T3,T4/T5,T6/T7,T8/T9, T10/T11,T12/L1 |
| Immune boosting | C5/C6,T6/T7,T8/T9,T12/L1,L2/L3 | C5/C6,T6/T7,T8/T9,T12/L1 L2/L3 |
| Sexual dysfunction | T2/T3,T10/T11,L2/L3,S1/S2 | T2/T3,T10/T11,L2/L3,S1/S2 |
| Attention deficit disorder | C1,C3/C4,T2/T3,T6/T7,T8/T9, T10/T11,S1/S2 | C1,C3/C4,T2/T3,T6/T7, T8/T9,T10/T11,S1/S2 |
| Insomnia | | T4/T5,T8/T9,L2/L3 |
| Obesity | | T10/T11,L2/L3,S1/S2 |
| Cervical vertebrae pain | C3/C4,C5/C6,T2/T3,T4/T5,T6/T7, T8/T9,T10/T11,T12/L1,L2/L3, L4/L5,S1/S2,S2/S3 | |
| Lumbar disc | C3/C4,C5/C6,C7/T1,T2/T3,T4/T5, T6/T7,T8/T9,T10/T11,T12/L1, L2/L3,L4/L5,S1/S2,S2/S3,S3/S4 | |

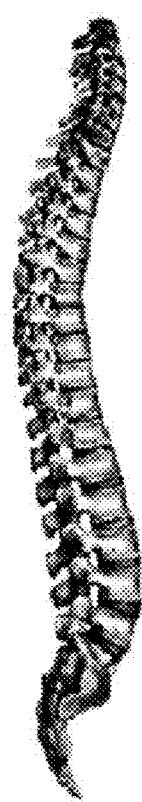
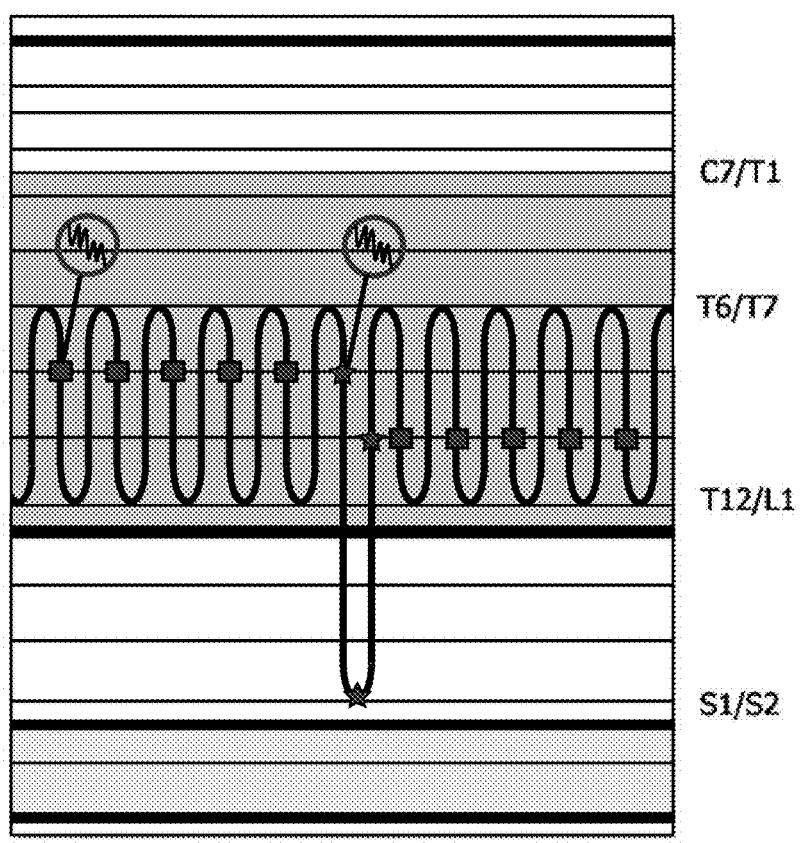
FIG. 13A

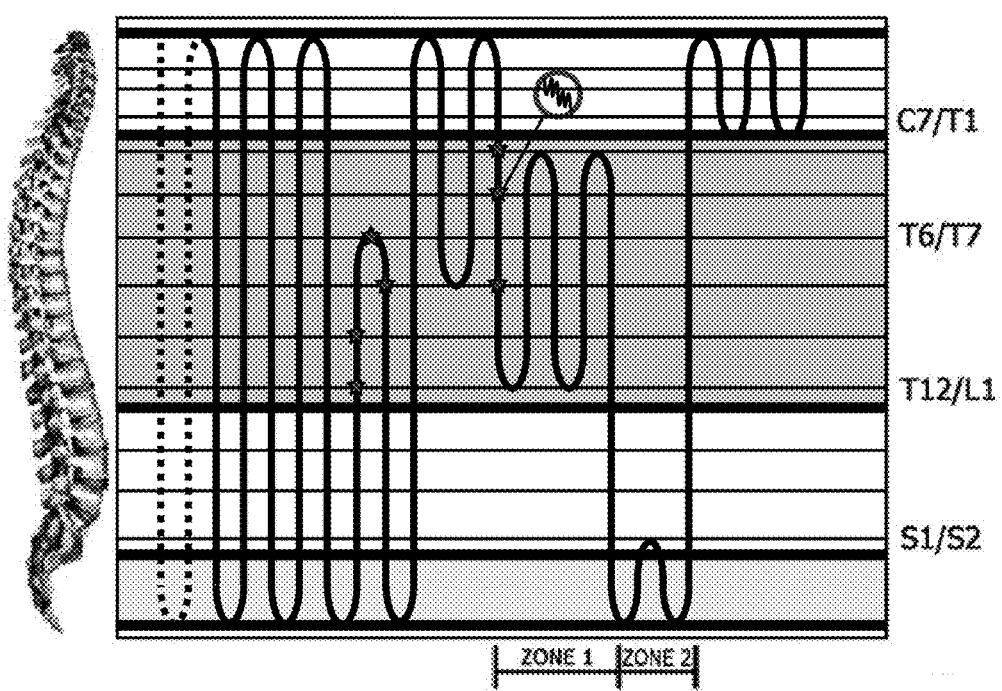

METHOD FOR SETTING MASSAGE PATTERN OF THERMOTHERAPY DEVICE

CROSS-REFERENCE TO RELATED APPLICATIONS

This application is the U.S. national phase application filed under 35 U.S.C. § 371 claiming benefit to International Patent Application No. PCT/KR2012/008784, filed on Oct. 24, 2012, which is entitled to priority under 35 U.S.C. § 119(a)-(d) to Korea application nos. 10-2011-0109022, filed Oct. 24, 2011; 10-2011-0109023, filed Oct. 24, 2011; 10-2011-0109024, filed Oct. 24, 2011 and 10-2011-0109025, filed Oct. 24, 2011, each of which application is hereby incorporated herein by reference in its entirety.

TECHNICAL FIELD

The present invention relates to a method for setting a massage pattern of a thermotherapy device, and, more particularly, to a method for setting a massage pattern of a thermotherapy device capable of patterning movement of a moxibustion device according to a disease to intensively perform a massage on vertebrae associated with the disease, and thus allowing a motor to drive the moxibustion device according to a massage pattern set to automatically perform a customized massage according to a disease when the disease is selected.

BACKGROUND ART

The central nerves of a human body go through the spine to body parts, and thus main meridian points associated with activities of various organs such as the heart, lungs, and stomach as well as various adult diseases are scattered around the spine. Accordingly, acupressure or moxibustion has been widely carried out on spine meridian points together with acupuncture in Oriental medicine to strengthen immune functions, or relieve physical pains, and treat and prevent diseases. In recent years, thermotherapy devices have prevailed for use in general homes for the purpose of these therapeutic effects.

In general, a thermotherapy device configured to treat diseases at the spine with acupressure and warmth serves to simulate meridian systems and meridian points positioned around the spine while forcing an acupressure ball provided with a lamp to move in a horizontal direction. In this case, far-infrared rays emitted from the lamp have an acupuncture effect since they function to penetrate deep into the skin, the warmth has a moxibustion effect, and the acupressure ball has an acupressure effect.

However, conventional thermotherapy devices have problems because they use the concept of simply massaging the spine for health, and do not carry out more specific and elaborate massages for health according to diseases and health conditions of an individual, and a desired therapeutic effect.

That is, the conventional thermotherapy devices have a problem in that a therapeutic effect is not expressed in users who want a more specified massage such as users having a poor digestive system or suffering from obesity or insomnia since all of them get a massage according to the same general customized massage pattern.

DISCLOSURE

Technical Problem

Accordingly, the present invention is designed to solve the problems of the prior art, and therefore it is an object of the present invention to provide a method for setting a massage pattern of a thermotherapy device capable of being applicable to thermotherapy according to specified and detailed massage patterns that are suitable for a user by setting a customized massage pattern according to a disease of the user.

It is another object of the present invention to provide a method for setting a massage pattern of a thermotherapy device capable of being applicable to thermotherapy according to specified and detailed massage patterns that are suitable for a user by setting a customized massage pattern according to a disease of the user so that a sympathetic nerve zone and a parasympathetic nerve zone into which an autonomic nerve zone is divided according to distribution of the peripheral nerves can be marked to intensively perform a massage on the related sympathetic and parasympathetic nerve zones according to the disease.

It is still another object of the present invention to provide a method for setting a moxibustion/acupressure pattern of a thermotherapy device capable of enabling moxibustion and acupressure for the purpose of treatment of a disease by setting moxibustion points and acupressure points around articulation points between vertebrae according to the disease and setting a moxibustion pattern and an acupressure pattern to perform moxibustion and acupressure when the moxibustion device reaches the moxibustion points and the acupressure points while being forced to move along a predetermined moving path.

It is yet another object of the present invention to provide a method for setting a massage mode of a thermotherapy device capable of effectively performing a massage for the purpose of treatment of a disease by setting a total massage time to be divided into a scanning mode, a standby mode, a treatment mode, and a finishing mode and performing massages in a sequential order while forcing a moxibustion device to move according to a pattern set in each mode upon massaging.

Technical Solution

To solve the above problem of the prior art, according to an aspect of the present invention, there is provided a method for setting a massage pattern of a thermotherapy device including a moxibustion device, a motor, a transfer unit, a controller, an input unit, and a memory unit. Here, the method includes a first operation of driving the moxibustion device to scan the entire spine of a user, setting articulation points between vertebrae as reference points for the human spine composed of cervical vertebrae, thoracic vertebrae, lumbar vertebrae, and a sacrum/coccyx, and storing the articulation point in the memory unit at the controller, a second operation of receiving information on related vertebrae according to human diseases or desired therapies, and storing the information in the memory unit at the controller, a third operation of receiving information on a moving path on which the moxibustion device actually moves with respect to the reference points while performing a massage on the vertebrae, receiving information on what times the moxibustion device repeatedly performs the massage while moving along the moving path, setting a massage pattern according to the human diseases or the desired therapies, and storing the massage pattern in the memory unit at the controller, and a fourth operation of searching for the corresponding massage pattern, receiving the corresponding massage pattern from the memory unit, and controlling the moxibustion device and the motor to perform a massage according to the set massage pattern at the controller when a diseases or a desired therapy is input through the input unit.

According to another aspect of the present invention, there is provided a method for setting a massage pattern of a thermotherapy device including a moxibustion device, a motor, a transfer unit, a controller, an input unit, and a memory unit. Here, the method includes a first operation of driving the moxibustion device to scan the entire spine of a user, setting articulation points between vertebrae as reference points for the human spine composed of cervical vertebrae, thoracic vertebrae, lumbar vertebrae, and a sacrum/coccyx, and storing the articulation point in the memory unit at the controller, a second operation of dividing an autonomic nerve zone into a sympathetic nerve zone and a parasympathetic nerve zone with respect to the reference points according to distribution of the peripheral nerves of the spine, and storing the sympathetic nerve zone and the parasympathetic nerve zone in the memory unit at the controller, a third operation of receiving information on a relationship between a disease sympathetic and parasympathetic nerves, and storing the information in the memory unit at the controller, a fourth operation of receiving information on a moving path on which the moxibustion device actually moves while performing a massage on the sympathetic nerve zone and/or the parasympathetic nerve zone in the case of a disease showing a relationship between the sympathetic nerves and the parasympathetic nerves, receiving information on what times the moxibustion device repeatedly performs the massage while moving along the moving path to set a massage pattern, and storing the massage pattern at the controller, and a fifth operation of searching for a massage pattern, receiving the massage pattern from the memory unit, and controlling the moxibustion device and the motor to perform a massage according to the set massage pattern at the controller when information on the disease showing the relationship between the sympathetic nerves and the parasympathetic nerves is input through the input unit.

According to still another aspect of the present invention, there is provided a method for setting a moxibustion/acupressure pattern of a thermotherapy device including a moxibustion device, a motor, a transfer unit, a controller, an input unit, and a memory unit. Here, the method includes a first operation of driving the moxibustion device to scan the entire spine of a user, setting articulation points between vertebrae as reference points for the human spine composed of cervical vertebrae, thoracic vertebrae, lumbar vertebrae, and a sacrum/coccyx, and storing the articulation point in the memory unit at the controller, a second operation of receiving information on positions of related moxibustion points and acupressure points according to human diseases or desired therapies, and storing the information in the memory unit at the controller, a third operation of receiving information on a moxibustion intensity, a moxibustion temperature, and a moxibustion time for the moxibustion points, setting a moxibustion pattern, and storing the moxibustion pattern in the memory unit at the controller, a fourth operation of receiving information on an acupressure intensity, an acupressure time, and an acupressure type for the acupressure points, setting an acupressure pattern, and storing the acupressure pattern in the memory unit at the controller, and a fifth operation of searching for the corresponding moxibustion pattern and acupressure pattern, receiving the corresponding moxibustion pattern and acupressure pattern from the memory unit, and controlling the moxibustion device and the motor to perform moxibustion and acupressure according to the moxibustion pattern and the acupressure pattern at the controller when the moxibustion device reaches the reference points at which predetermined moxibustion points and acupressure points are positioned as moxibustion device is performing a massage while moving on a moving path when a disease is selected through the input unit.

According to yet another aspect of the present invention, there is provided a method for setting a massage mode of a thermotherapy device comprising a moxibustion device, a motor, a moving unit, a controller, an input unit, and a memory unit. Here, the method includes a first operation of performing a scanning mode at the controller, wherein the scanning mode is performed by driving the moxibustion device to scan the entire spine of a user, setting articulation points between vertebrae as reference points for the human spine composed of cervical vertebrae, thoracic vertebrae, lumbar vertebrae, and a sacrum/coccyx, and storing the articulation point in the memory unit, a second operation of receiving patterns in which tension applied to all spinal nerves or muscles is eased so that the spine sufficiently endures massage stimuli without any pain, combining the patterns to set a standby mode, and storing the standby mode in the memory unit at the controller, a third operation of receiving predetermined patterns based on vertebrae, moxibustion points and acupressure points, all of which are associated with a disease, in order to treat the disease, combining the patterns to set a treatment mode, and storing the treatment mode in the memory unit at the controller, a fourth operation of receiving patterns for inducing balancing of autonomic nerves and normalizing a user's condition so that a user can live a normal life after the massage, combining the patterns to set a finishing mode, and storing the finishing mode in the memory unit at the controller, and a fifth operation of controlling the motor and the moxibustion device in a sequential order at the controller according to the scanning mode, the standby mode, the treatment mode, and the finishing mode when information on a disease or desired therapy is input through the input unit.

Advantageous Effects

As described above, the method for setting a massage pattern of a thermotherapy device according to the present invention can be useful in performing a customized massage for each individual and exhibiting a better therapeutic effect on diseases since users can get a massage under the control of a thermotherapeutic system according to different diseases, health conditions, and desired therapies for each individual by setting reference points for setting a massage pattern, determining vertebrae associated with each disease and setting a massage pattern in which a massage can be performed on the vertebrae with respect to the reference points.

Also, the method for setting a massage pattern of a thermotherapy device according to a disease according to the present invention can be useful in performing a customized massage for each individual and exhibiting a better therapeutic effect on diseases since users can get a massage under the control of a thermotherapeutic system according to different diseases, health conditions, and desired therapies for each individual by setting a customized massage pattern so that a sympathetic nerve zone and a parasympathetic nerve zone into which an autonomic nerve zone is divided according to distribution of the peripheral nerves can be marked to intensively perform a massage on the related sympathetic and parasympathetic nerve zones according to the disease.

In addition, the method for setting a moxibustion/acupressure pattern of a thermotherapy device according to the present invention can be useful in performing customized moxibustion and acupressure for each individual and exhibiting a better therapeutic effect on diseases since users can get moxibustion and acupressure under the control of a thermotherapeutic system according to different diseases, health conditions, and desired therapies for each individual by setting moxibustion points and acupressure points around articulation points between vertebrae according to a disease and setting a moxibustion pattern and an acupressure pattern to perform moxibustion and acupressure when the moxibustion device reaches the moxibustion points and the acupressure points while being forced to move along a predetermined moving path.

Further, the method for setting a massage mode of a thermotherapy device according to the present invention can be useful in performing a massage for each individual and exhibiting a better therapeutic effect on diseases since users can get a massage under the control of a thermotherapeutic system according to different diseases, health conditions, and desired therapies for each individual by setting a total massage time to be divided into a scanning mode, a standby mode, a treatment mode, and a finishing mode and performing massages in a sequential order while causing a moxibustion device to move according to a pattern set in each mode upon massaging.

DESCRIPTION OF DRAWINGS

FIG. 4 is a diagram showing one exemplary embodiment an associative relation between a disease and vertebrae according to the present invention.

FIG. 12 is a diagram explaining one exemplary embodiment of an associative relation between a disease and moxibustion points and acupressure points according to the present invention.

FIG. 13 is a diagram showing one exemplary embodiment of a moxibustion/acupressure pattern according to a disease according to the present invention.

BEST MODE

Hereinafter, the present invention configured thus will be described in detail referring to the accompanying drawings.

Figure 1:
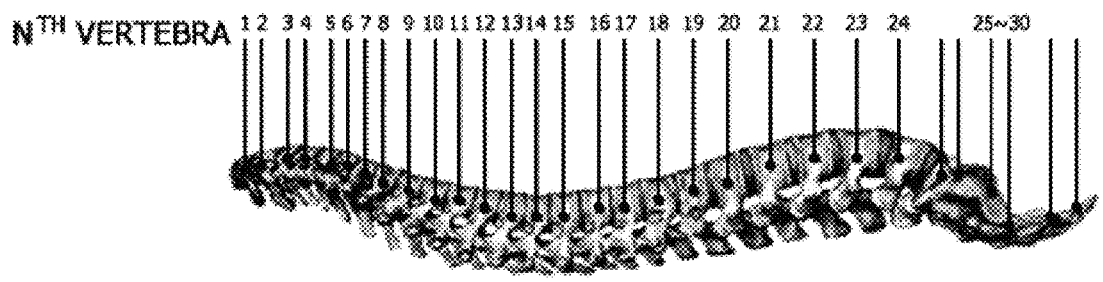
FIG. 1 is a diagram showing a typical human spine.

FIG. 1 is a diagram showing a typical human spine. The spine is mainly divided into cervical vertebrae, thoracic vertebrae, lumber vertebrae, and a sacrum/coccyx. As shown in FIG. 1, the cervical vertebrae are the $1^{st}$ to $7^{th}$ vertebrae, and are associated with autonomic nervous functions in headaches, insomnia, optic nerves, ear diseases, teeth, dizziness, and the like. The thoracic vertebrae are the $8^{th}$ to $19^{th}$ vertebrae, and are closely associated with autonomic nervous functions in heart functions, digestive functions, contraction of blood vessels, internal diseases, and the like. The lumbar vertebrae are the $20^{th}$ to $24^{th}$ vertebrae, and are closely associated with autonomic nervous functions in colitis, diarrhea, constipation, lower quadrant pain, backaches, sciatic neuralgia, the prostate, bladder diseases, and the like. The sacrum/coccyx includes the $25^{th}$ to $30^{th}$ vertebrae, which are closely associated with autonomic nervous functions in reproductive organs, the prostate, hemorrhoids, the rectum, and the like.

Example 1

Figure 2:
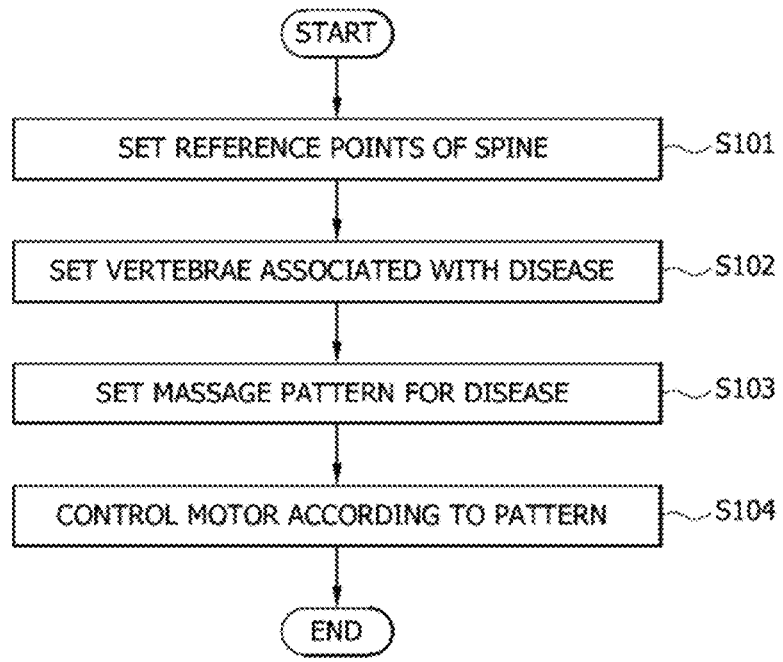
FIG. 2 is a diagram showing a flowchart for setting a massage pattern according to the present invention.

FIG. 2 is a diagram showing a flowchart for setting a massage pattern.

Figure 3:
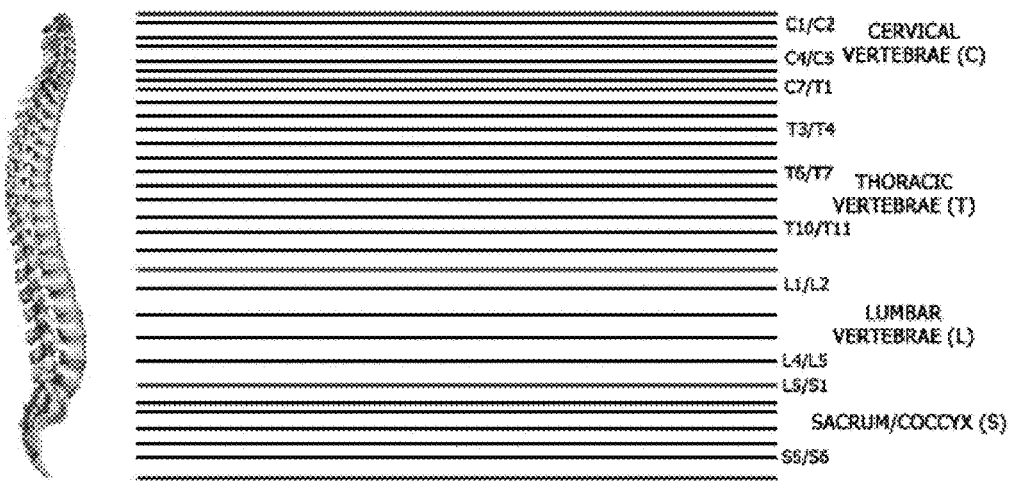
FIG. 3 is a diagram showing one exemplary embodiment of reference points for setting a massage pattern according to the present invention.

As the first operation, first of all, reference points are set for the entire spine, and stored to set a massage pattern (S101). First, a moxibustion device is driven to scan the entire spine of a user, positions of the vertebrae are determined, and articulation points between the vertebrae are set as the reference points. This is because nerve fascicles are present at the articulation points between the vertebrae. The reference points are points for establishing landmarks to set a massage pattern. In this case, the reference points become starting points and end points of massage patterns. When the massage pattern is set, all of the reference points need not be shown, and some reference points may be optionally deleted, with only some important reference points shown. FIG. 3 is a diagram showing one exemplary embodiment of reference points for setting a massage pattern. As shown in FIG. 3, the vertebrae are divided into cervical vertebrae C, thoracic vertebrae T, lumbar vertebrae L, and the sacrum/coccyx S, and the numbers in the spine represent the order of the vertebrae. For example, the term "C1/C2" refers to an articulation point between the $1^{st}$ and $2^{nd}$ cervical vertebrae. Similarly, the term "T1/T2" refers to an articulation point between the $1^{st}$ and $2^{nd}$ thoracic vertebrae. Therefore, the cervical vertebrae have 7 reference points of C1, C1/C2, C2/C3, C3/C4, C4/C5, C5/C6, and C6/C7, the thoracic vertebrae have 12 reference points of C7/T1, T1/T2, T2/T3, T3/T4, T4/T5, T5/T6, T6/T7, T7/T8, T8/T9, T9/T10, T10/T11, and T11/T12, the lumbar vertebrae has 5 reference points of T12/L1, L1/L2, L2/L3, L3/L4, and L4/L5, and the sacrum/coccyx has 6 reference points of L5/S1, S1/S2, S2/S3, S3/S4, S4/S5, and S5.

As the second operation, information on vertebrae associated with a disease is received and stored (S102). Related organs, muscles, or body parts are determined according to a user's disease or desired therapy. When the organs, muscles, or body parts are determined, the vertebrae corresponding to the organs, muscles or body parts are determined FIG. 4 is a diagram explaining one exemplary embodiment of an associative relation between a disease and vertebrae. In the case of dyspepsia, for example, the related body organs are the spleen, the stomach, the liver, the gall bladder, and the small intestine, and the related vertebrae are thoracic vertebra 9 (T9), thoracic vertebra 10 (T10), thoracic vertebra 11 (T11), thoracic vertebra 12 (T12), and sacrum/coccyx 1 (S1). In the case of obesity, the related organs are the spleen, the kidney, and the small intestine, and the related vertebrae are thoracic vertebra 4 (T4) through thoracic vertebra 12 (T12), lumbar vertebra 2 (L2), and sacrum/coccyx 1 (S1).

Figure 5B:
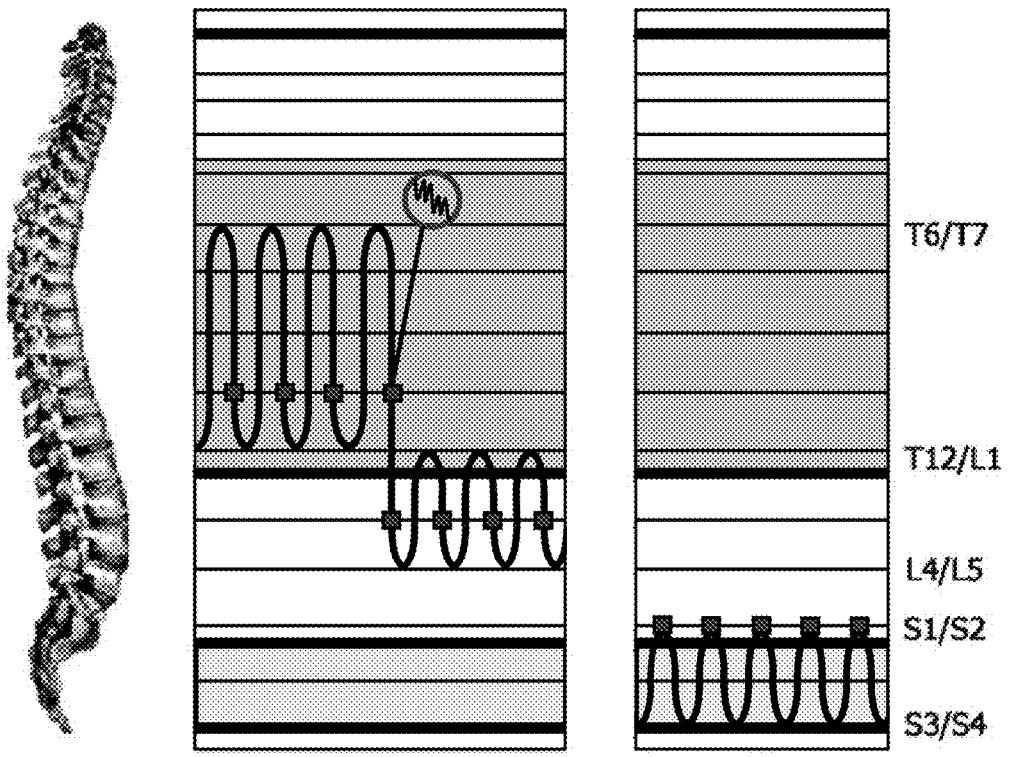
FIG. 5 is a diagram showing one exemplary embodiment of a massage pattern according to a disease according to the present invention.

The third operation is to set a massage pattern according to a disease and store the massage pattern (S103). As described above, when the vertebrae to be massaged are determined according to each disease or desired therapy, a moving path on which the moxibustion device actually moves with respect to the reference points while performing a massage on the vertebrae to be massaged is set, and stored. Information on what times the moxibustion device repeatedly performs the massage while moving along the moving path is input. Also, when the moxibustion device performs a massage while moving, a moving speed, a massage pressure, and a device temperature of the moxibustion device are set and input. As described above, a detailed massage pattern is set by determining a moving path of the moxibustion device, a movement repeat count, a moving speed, a massage pressure, and a temperature of the moxibustion device. When the detailed massage pattern is set as described above, a motor configured to drive the moxibustion device is controlled according to the detailed massage pattern to force the moxibustion device to perform a massage. Such a massage pattern may be present in a plural number for a disease. FIG. 5 is a diagram showing one exemplary embodiment of a massage pattern according to a disease. Referring to FIG. 5A, vertebrae associated with dyspepsia are T9, T10, T11, T12, and S1. Thus, a detailed massage pattern in which T9, T10, T11, T12, and S1 are intensively massaged for a user who wants a massage because of dyspepsia is set. The first massage pattern is set with 6 repeated stroke massages from a reference point T6/T7 to a reference point T12/L1, a "middle" moving speed, a "strong" massage pressure, and a moxibustion device temperature of 55° C., the second massage pattern is set with one stroke T8/T9 from a reference point T6/T7 to a reference point S1/S2, a "middle" moving speed, a "strong" massage pressure, and a moxibustion device temperature of 45° C., and the third massage pattern is set with 5 repeated strokes from a reference point T6/T7 to a reference point T12/L1, a "middle" moving speed, a "strong" massage pressure, and a moxibustion device temperature of 50° C. Referring to FIG. 5B, a detailed massage pattern in which T4 to T12, L2, and S1 are intensively massaged for a user who wants a massage because of obesity is set. The first massage pattern is set with 4 repeated strokes from reference points T4/T5 to T12/L1, a "high" moving speed, a "strong" massage pressure, and a moxibustion device temperature of 55° C., the second massage pattern is set with 4 strokes from reference points T12/L1 to L4/L5, a "slow" moving speed, a "weak" massage pressure, and a moxibustion device temperature of 55° C., and the third massage pattern is set with 5 repeated strokes from reference points S1/S2 to S3/S4, a "middle" moving speed, a "strong" massage pressure, and a moxibustion device temperature of 50° C.

The fourth operation is to control the moxibustion device and the motor according to the set massage pattern when information on a disease or desired therapy is input from the input unit (S104). The set massage pattern is stored in the memory unit, and the controller receives a massage pattern from the memory unit, and controls the moxibustion device and the motor to perform a massage according to the set massage pattern. The controller transmits a signal value to the motor to control a massage moving path, a repeat count, a moving speed, and a massage pressure in the massage pattern, and transmits a signal value to the moxibustion device to control a temperature of the moxibustion device.

Figure 6:
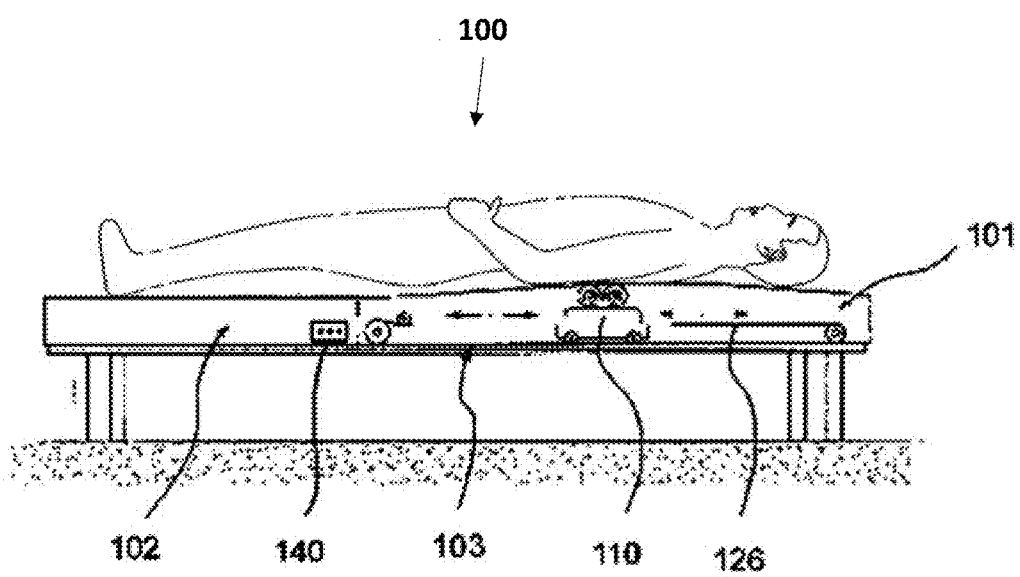
FIG. 6 is a side view showing one exemplary embodiment of a thermotherapy device according to the present invention.

FIG. 6 is a side view schematically showing an internal configuration of a thermotherapy device according to the present invention.

A thermotherapy device 100 basically includes a main mat 101 used for a user's upper body and a spinal area of the upper body, and an auxiliary mat 102 used for a user's lower body area. Also, the thermotherapy device 100 may include a loading unit 103 configured to support the main mat and the auxiliary mat put thereon, as necessary. The thermotherapy device 100 is provided with a moxibustion device 110 moving toward the spine of a user in order to provide thermotherapeutic fomentation and thermotherapeutic massage effects to a user's body area (especially a user's back area). The moxibustion device 110 provides the thermotherapeutic fomentation and thermotherapeutic massage effects to the user using high heat and far-infrared rays generated from electric energy supplied from a power source unit. The shape of the moxibustion device 110 includes both of a cap shape and a roller shape. Various shapes and structures may be used as the shape of the moxibustion device, but the present invention is not limited thereto. Such a moxibustion device includes a heat generating unit configured to generate heat using electric energy, and a heated section heated by the heat generating unit. In this Example, a lamp or an electric heater is used as the heat generating unit, and a far-infrared emitter such as jade is used as the heated section. However, various heating elements or materials and substances capable of being heated by application of heat may be used as such a heat generating unit and heated section.

The thermotherapy device 100 is provided with a motor 140 and a transfer unit 126 to enable the moxibustion device 110 to reciprocate in the thermotherapy device. The motor 140 rotates as electric energy is applied to the motor 140, and the transfer unit 126 is coupled to the motor 140 to provide a turning force a turning force of the motor 140 to translocate the moxibustion device with rotation of the motor 140. The transfer unit 126 is coupled to the moxibustion device 110, and used to translocate the moxibustion device 110 forwards or backwards (that is, one direction or a reverse direction) according to normal or reverse rotation of the motor 140. One of a transfer belt, a transfer chain and a transfer rope may be selectively used as the transfer unit 126. Of course, various systems configured to transfer an object using a driving force of the motor may be used herein, but the present invention is not limited thereto.

The thermotherapy device 100 includes a controller configured to control an operation of the thermotherapy device, an input unit configured to receive a user's operation signal and provide the operation signal to the controller, and a memory unit configured to store input information. The controller drives the moxibustion device to scan the entire spine of a user, sets articulation points between vertebrae as reference points for the human spine composed of cervical vertebrae, thoracic vertebrae, lumbar vertebrae, and a sacrum/coccyx, and stores the articulation points in the memory unit. Also, the controller receives information on related vertebrae according to human diseases or desired therapies, and stores the information in the memory unit. When the vertebrae to be massaged are determined according to each disease or desired therapy, the controller sets a moving path on which the moxibustion device actually moves with respect to the reference points while performing a massage on the vertebrae to be massaged, and stores the moving path in the memory unit. Then, the controller stores information on what times the moxibustion device repeatedly performs the massage while moving along the moving path, determines a moving speed, a massage pressure, and a temperature of the moxibustion device when the moxibustion device performs a massage while moving, and stores the moving speed, the massage pressure, and the temperature of the moxibustion device temperature. Also, when information on a disease or desired therapy is input through the input unit, the controller searches for the corresponding massage pattern, receives the corresponding massage pattern from the memory unit, and controls the moxibustion device and the motor to perform a massage according to the set massage pattern. In this Example, the controller may be one or a plurality of control chips or control elements mounted on one or a plurality of PCBs. Information on the reference points, information on the related vertebrae according to the human diseases or desired therapies, and information on the massage pattern including a moving path, a massage count, a moving speed of the moxibustion device, a massage pressure, and a temperature of the moxibustion device are stored in the memory unit for the user's spine. A user may use his/her hands to input necessary information through the input unit. Here, the input unit may be realized to have various wired or wireless structures.

Example 2

Figure 7:
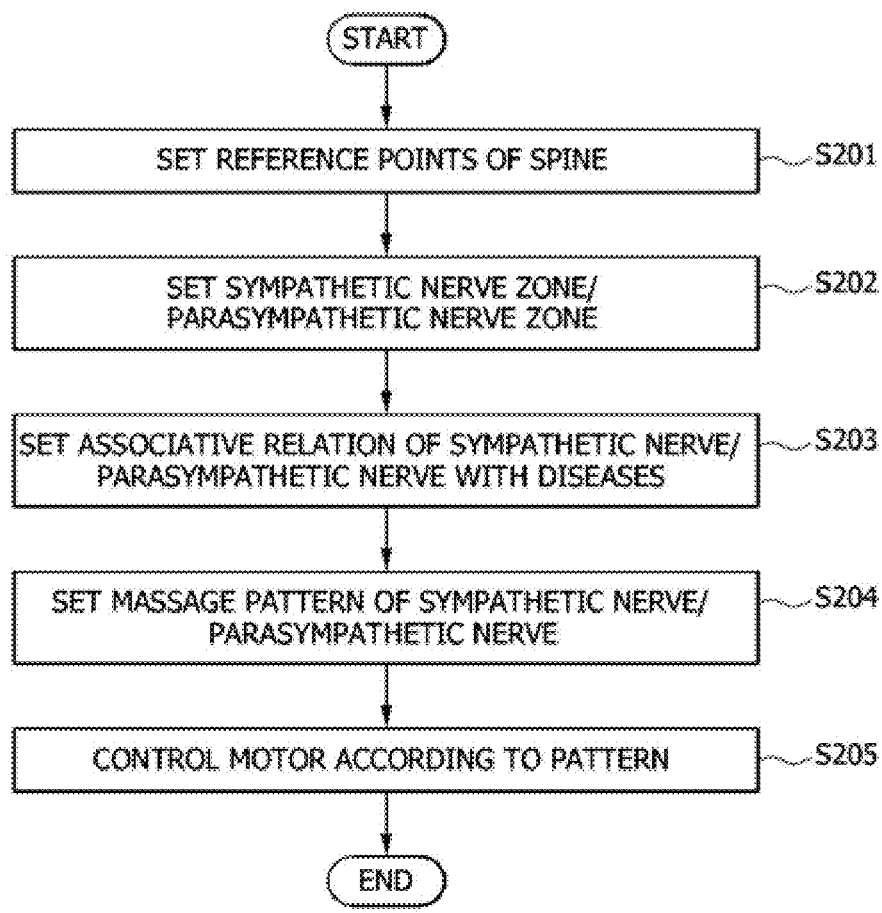
FIG. 7 is a diagram showing a flowchart for setting a massage pattern according to the present invention.

FIG. 7 is a diagram showing a flowchart explaining a massage pattern.

As the first operation, first of all, reference points are set for the entire spine, and stored to set a massage pattern (S201). First, the moxibustion device is driven to scan the entire spine of a user, positions of vertebrae are determined, and articulation points between the vertebrae are set as reference points. This is because nerve fascicles are present at the articulation points between the vertebrae. The reference points are points for establishing landmarks to set a massage pattern. In this case, the reference points become starting points and end points of massage patterns. When the massage pattern is set, all the reference points need not be shown, and some reference points may be optionally deleted, with only some important reference points shown. FIG. 3 is a diagram showing one exemplary embodiment of reference points for setting a massage pattern. As shown in FIG. 3, the vertebrae are divided into cervical vertebrae C, thoracic vertebrae T, lumbar vertebrae L, and a sacrum/coccyx S, and the numbers in the spine represent the order of the bones. For example, the term "C1/C2" refers to an articulation point between the $1^{st}$ and $2^{nd}$ cervical vertebrae. Similarly, the term "T1/T2" refers to an articulation point between the $1^{st}$ and $2^{nd}$ thoracic vertebrae. Therefore, the cervical vertebrae have 7 reference points of C1, C1/C2, C2/C3, C3/C4, C4/C5, C5/C6, and C6/C7, the thoracic vertebrae have 12 reference points of C7/T1, T1/T2, T2/T3, T3/T4, T4/T5, T5/T6, T6/T7, T7/T8, T8/T9, T9/T10, T10/T11, and T11/T12, the lumbar vertebrae have 5 reference points of T12/L1, L1/L2, L2/L3, L3/L4, and L4/L5, and the sacrum/coccyx has 6 reference points of L5/S1, S1/S2, S2/S3, S3/S4, S4/S5, and S5.

Figures 8, 9:
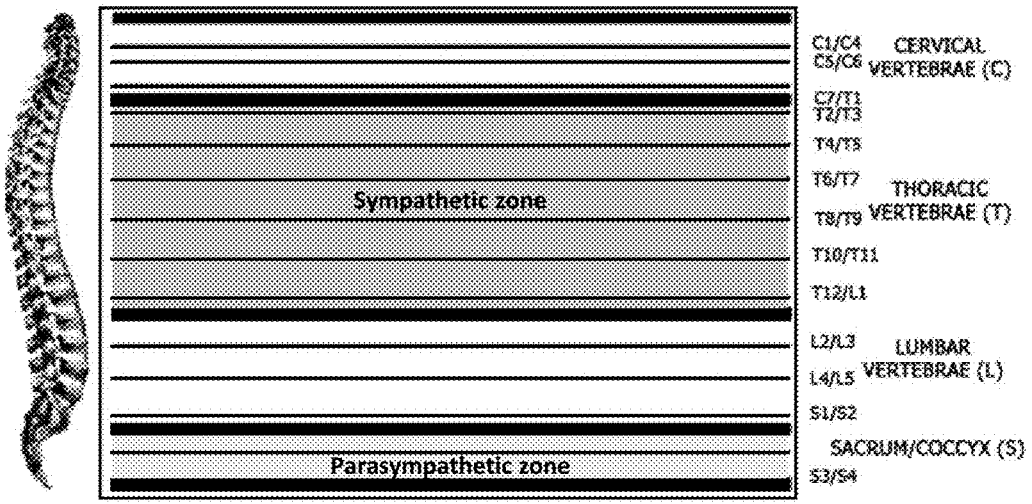
FIG. 8 is a diagram explaining one exemplary embodiment of a sympathetic nerve zone and a parasympathetic nerve zone according to the present invention.
FIG. 9 is a diagram explaining one exemplary embodiment of a relationship between sympathetic nerves and parasympathetic nerves according to a disease according to the present invention.

As the second operation, an autonomic nerve zone is divided into a sympathetic nerve zone and a parasympathetic nerve zone according to distribution of the peripheral nerves of the spine, and the sympathetic nerve zone and the parasympathetic nerve zone are stored (S202). There is a related autonomic nerve zone according to a user's disease or desired therapy. For this purpose, the autonomic nerve zone is divided into a sympathetic nerve zone and a parasympathetic nerve zone, and the sympathetic nerve zone and the parasympathetic nerve zone are stored. The sympathetic nerve zone and the parasympathetic nerve zone are determined based on the reference points. FIG. 8 is a diagram explaining one exemplary embodiment of the sympathetic nerve zone and the parasympathetic nerve zone. Referring to FIG. 8, the sympathetic nerve zone spans from T1/T2 to L1/L2, and the parasympathetic nerve zone spans from S2/S3 to S5.

The third operation is to receive information on a relationship between the sympathetic nerve and the parasympathetic nerve according to a disease, and store the information (S203). All blood vessels of a human body are controlled by nerves. In this case, the nerves are referred to as autonomic nerves, and sympathetic nerves and parasympathetic nerves in the autonomic nerves move contrary to each other. The sympathetic nerves are strained to shrink blood vessels and increase a blood pressure when a user feels a sense of tension, anxiety, or restlessness. On the other hand, the parasympathetic nerves are relaxed with expansion of blood vessels to decrease a blood pressure. FIG. 9 is a diagram showing one exemplary embodiment of a relationship between the sympathetic nerves and the parasympathetic nerves according to a disease. Referring to FIG. 9, diseases such as blood circulation disorders, immune boosting, insomnia, and obesity have a close relationship with the sympathetic nerves and/or parasympathetic nerves. Therefore, it is necessary to stimulate and relax the sympathetic nerves and/or parasympathetic nerves by performing a massage on the sympathetic nerve zones and/or parasympathetic nerve zones in order to treat such diseases.

Figure 10:
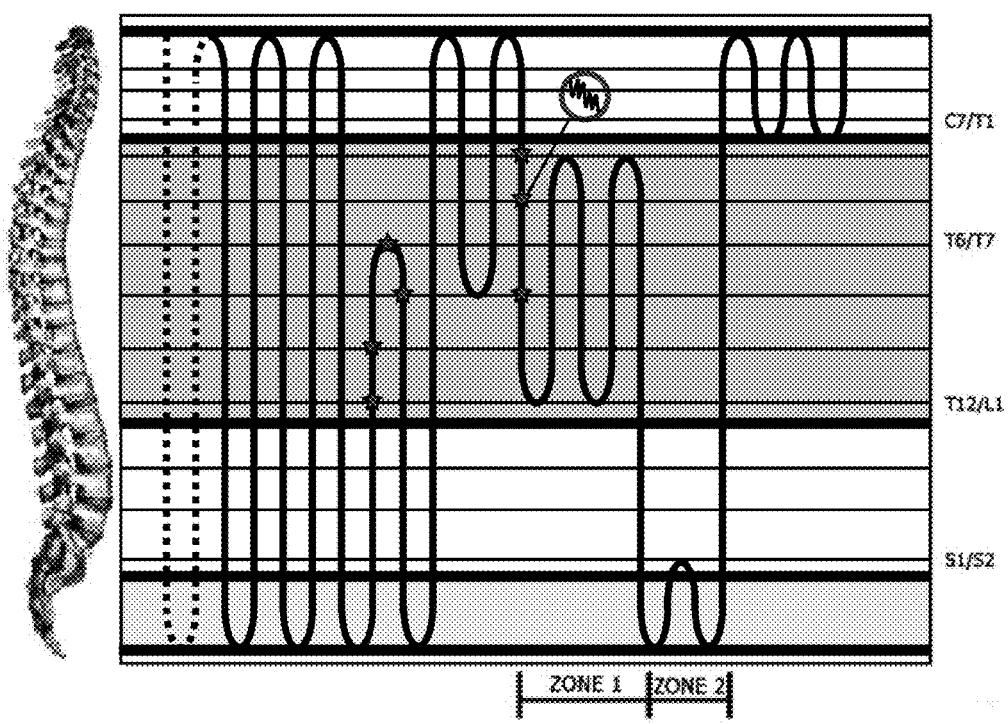
FIG. 10 is a diagram showing one exemplary embodiment of a massage pattern for the sympathetic nerves and the parasympathetic nerves according to a disease according to the present invention.

The fourth operation is to set a massage pattern for the sympathetic nerves and the parasympathetic nerves and store the massage pattern (S204). As described above, in the case of a disease showing a relationship between the sympathetic nerves and the parasympathetic nerves, a moving path on which the moxibustion device actually moves while performing a massage on the sympathetic nerve zones and the parasympathetic nerve zones is set and input. That is, it is determined what times the moxibustion device repeatedly performs a massage on the sympathetic nerve zone or the parasympathetic nerves. Also, when the moxibustion device performs the massage while moving, a moving speed, a massage pressure, and a temperature of the moxibustion device are set and stored. Also, when both of the sympathetic nerve zone and the parasympathetic nerve zone have to be massaged, the massage order determining which of the sympathetic nerve zone and the parasympathetic nerve zone is massaged first is input. As described above, the detailed massage pattern is set by determining a moving path of the moxibustion device, a movement repeat count, a moving speed, a massage pressure, a temperature of the moxibustion device, and a massage order. When the detailed massage pattern is set as described above, the motor configured to drive the moxibustion device is controlled according to the detailed massage pattern so that the moxibustion device can perform a massage. Generally, the temperature of the moxibustion device for sympathetic nerve massages is higher than that of the moxibustion device for parasympathetic nerve massages, and the massage pressure to the sympathetic nerves is stronger than that to the parasympathetic nerves. Also, when both the sympathetic nerve zone and the parasympathetic nerve zone have to be massaged, the sympathetic nerves may be massaged, and the parasympathetic nerves may be massaged with low stimuli to prevent overloading of the activated sympathetic nerves. FIG. 10 is a diagram showing one exemplary embodiment of a massage pattern for the sympathetic nerves and the parasympathetic nerves according to a disease. Referring to FIG. 10, in the massage pattern associated with blood circulation, Zone 1 represents a massage pattern for the sympathetic nerves, and is set with two repeated stroke massages on the sympathetic nerve zone, a "middle" moving speed, a "strong" massage pressure, and a moxibustion device temperature of 65° C., and Zone 2 represents a massage pattern for the parasympathetic nerves, and is set with two repeated stroke massages on the parasympathetic nerve zone, a "low" moving speed, a "weak" massage pressure, and a moxibustion device temperature of 45° C.

The fifth operation is to control the motor according to the set massage pattern for the sympathetic nerves and the parasympathetic nerves (S205). The set massage pattern is stored in the memory unit, and when information on a disease showing a relationship between the sympathetic nerves and the parasympathetic nerves is input through the input unit, the controller receives a massage pattern from the memory unit, and controls the moxibustion device and the motor to perform a massage according to the massage pattern. In this case, the controller transmits a signal value to the motor to control a massage moving path, a repeat count, a moving speed, and a massage pressure in the massage pattern, and also transmits a signal value to the moxibustion device to control a temperature of the moxibustion device.

Example 3

Figure 11:
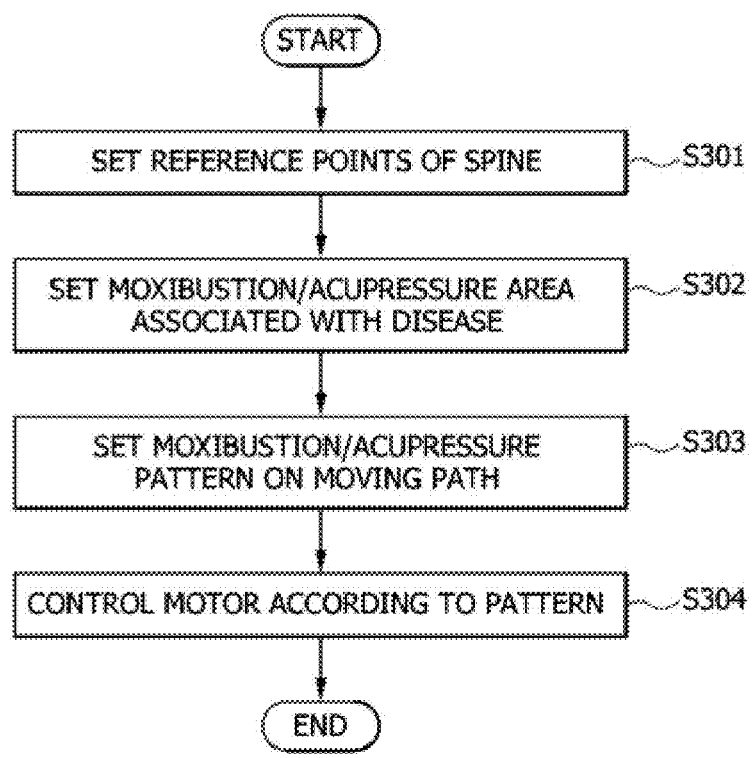
FIG. 11 is a diagram showing a flowchart for setting a moxibustion/acupressure pattern according to the present invention.

FIG. 11 is a diagram showing a flowchart explaining a moxibustion/acupressure pattern.

As the first operation, first of all, reference points are set for the entire spine and stored to set a moxibustion/acupressure pattern (S301). First, the moxibustion device is driven to scan the entire spine of a user, positions of vertebrae are determined, and articulation points between the vertebrae are set as reference points. This is because nerve fascicles are present at the articulation points between the vertebrae. In this case, the above-described articulation points become moxibustion points and acupressure points. When the moxibustion/acupressure pattern is set, all the reference points need not be shown, and some reference points may be optionally deleted, with only some important reference points shown. FIG. 3 is a diagram showing one exemplary embodiment of reference points for setting a moxibustion/acupressure pattern. As shown in FIG. 3, the vertebrae are divided into cervical vertebrae C, thoracic vertebrae T, lumbar vertebrae L, and a sacrum/coccyx S, and the numbers in the spine represent the order of the bones. For example, the term "C1/C2" refers to an articulation point between the $1^{st}$ and $2^{nd}$ cervical vertebrae. Similarly, the term "T1/T2" refers to an articulation point between the $1^{st}$ and $2^{nd}$ thoracic vertebrae. Therefore, the cervical vertebrae have 7 reference points of C1, C1/C2, C2/C3, C3/C4, C4/C5, C5/C6, and C6/C7, the thoracic vertebrae have 12 reference points of C7/T1, T1/T2, T2/T3, T3/T4, T4/T5, T5/T6, T6/T7, T7/T8, T8/T9, T9/T10, T10/T11, and T11/T12, the lumbar vertebrae have 5 reference points of T12/L1, L1/L2, L2/L3, L3/L4, and L4/L5, and the sacrum/coccyx has 6 reference points of L5/S1, S1/S2, S2/S3, S3/S4, S4/S5, and S5.

As the second operation, moxibustion points and acupressure points associated with a disease are received and stored (S302). The related moxibustion points and acupressure points are determined according to a user's disease or desired therapy. FIG. 12 is a diagram explaining one exemplary embodiment of an associative relation between a disease and moxibustion points and acupressure points. In the case of dyspepsia, for example, the related moxibustion points and acupressure points are T8/T9, T10/T11, and S1/S2. In the case of obesity, the related acupressure points are also T10/T11, L2/L3, and S1/S2, and there are no moxibustion points. In the case of lumbar disc, the related moxibustion points are C3/C4, C5/C6, C7/T1, T2/T3, T4/T5, T6/T7, T8/T9, T10/T11, T12/L1, L2/L3, L4/L5, S1/S2, S2/S3, and S3/S4, and there are no acupressure points.

The third operation is to set and store a moxibustion/acupressure pattern according to a disease (S303). When the moxibustion device reaches the reference points at which predetermined moxibustion points and acupressure points are positioned as the moxibustion device is actually performing a massage according to each disease or desired therapy while moving along a moving path, a moxibustion intensity, a moxibustion temperature, a moxibustion time, an acupressure intensity, an acupressure time, and an acupressure type for moxibustion and acupressure are determined and input. As described above, the moxibustion/acupressure pattern is set by determining positions of the moxibustion points, a moxibustion intensity, a moxibustion temperature, a moxibustion time, positions of acupressure points, an acupressure intensity, an acupressure time, and an acupressure type. The acupressure type represents an operation type of the moxibustion device upon acupressure, and thus may be divided into a horizontal vibration type, a vertical vibration type, a rotation type, and a combination thereof. When the detailed moxibustion/acupressure pattern is set as described above, the motor configured to drive the moxibustion device is controlled according to the detailed moxibustion/acupressure pattern to perform moxibustion and acupressure. A time required to translocate the moxibustion device so as to treat a disease is mainly composed of a scanning mode, a standby mode, a treatment mode, and a finishing mode, and the moxibustion/acupressure pattern is achieved in the treatment mode in which the moxibustion device moves to treat a disease. FIG. 13 is a diagram showing one exemplary embodiment of a moxibustion/acupressure pattern according to a disease. Referring to FIG. 13A, moxibustion points and acupressure points associated with dyspepsia are T8/T9, T10/T11, and S1/S2. Thus, a detailed moxibustion/acupressure pattern is set to perform intensive moxibustion and acupressure on T8/T9, T10/T11, and S1/S2 for a user who wants a massage because of dyspepsia is set. The first moxibustion/acupressure pattern is set with a "strong" moxibustion intensity at a reference point T8/T9, a moxibustion time of 100 seconds, a moxibustion temperature of 65° C., a "strong" acupressure intensity, an acupressure time of 150 seconds, and a vertically reciprocating acupressure type, the second moxibustion/acupressure pattern is set with a "strong" moxibustion intensity at a reference point T10/T11, a moxibustion time of 100 seconds, a moxibustion temperature of 65° C., a "strong" acupressure intensity, an acupressure time of 150 seconds, and a combined acupressure type, and the third moxibustion/acupressure pattern is set with a "strong" moxibustion intensity at a reference point S1/S2, a moxibustion time of 200 seconds, a moxibustion temperature of 60° C., a "strong" acupressure intensity, an acupressure time of 150 seconds, and a rotating acupressure type. Referring to FIG. 13B, a user who wants a massage because of obesity gets no moxibustion, and a detailed acupressure pattern is set to perform acupressure on T10/T11, L2/L3, and S1/S2. The first acupressure pattern is set with a "strong" acupressure intensity at a reference point T10/T1, and an acupressure time of 120 seconds, the second acupressure pattern is set with a "middle" acupressure intensity at a reference point L2/L3, and an acupressure time of 150 seconds, and the third acupressure pattern is set with "strong" acupressure intensity at a reference point S1/S2, an acupressure time of 200 seconds, and a combined acupressure type.

The fourth operation is to control the motor according to the set moxibustion/acupressure pattern (S304). The set moxibustion/acupressure pattern is stored in the memory unit, and the controller receives a moxibustion/acupressure pattern from the memory unit, and controls the moxibustion device and the motor to perform moxibustion and acupressure according to the set moxibustion/acupressure pattern. In this case, the controller transmits a signal value to the motor to control positions of the moxibustion points, a moxibustion intensity, a moxibustion time, positions of the acupressure points, an acupressure intensity, an acupressure time, and an acupressure type in the moxibustion/acupressure pattern, and transmits a signal value to the moxibustion device control a moxibustion temperature.

Example 4

Figure 14:
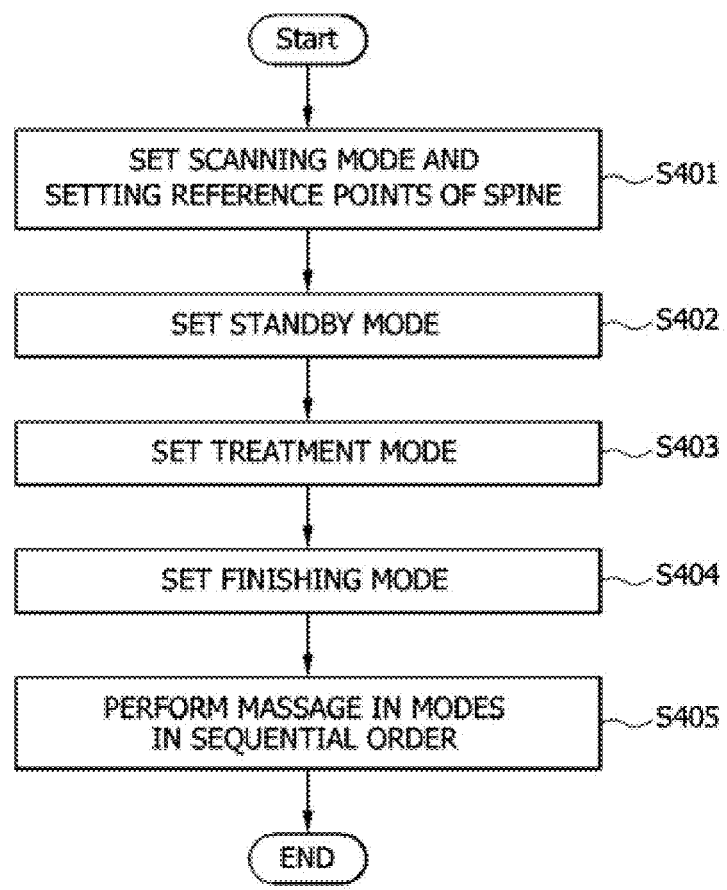
FIG. 14 is a diagram showing a flowchart for setting a massage mode according to the present invention.

FIG. 14 is a diagram showing a flowchart explaining a massage mode.

As the first operation, a scanning mode is set, and reference points of the spine are set and stored based on the results of the scanning mode (S401). Since users carrying the thermotherapy device have different body types, the users have different reference points. Therefore, the scanning mode is a mode which is first carried out in the total massage time, and in which the entire spine of a user is scanned to determine exact positions of the vertebrae. Therefore, articulation points between the vertebrae are set as reference points based on the positions of the vertebrae recognized through the scanning mode. The scanning mode typically has a single pattern for the entire spine.

As the second operation, a standby mode is set and stored (S402). The standby mode is a mode for easing tension of all spinal nerves or muscles so as to create an environment in which the spine sufficiently endures massage stimuli without any pain in a subsequent treatment mode. Thus, the standby mode is composed of an ease pattern in which soft stimuli are applied to the entire spine, a strengthening pattern in which strong stimuli are applied to the entire spine, and the like.

The third operation is to set and store a treatment mode (S403). The treatment mode is a mode for performing a massage or moxibustion and acupressure on vertebrae associated with a disease so as to treat the disease. Thus, the treatment mode has a specified pattern for treating a disease. The kinds of patterns that may be selected in the treatment mode include an intensive pattern in which a massage is intensively performed on vertebrae associated with a disease, a whole pattern in which a massage is performed on the entire spine, an area pattern in which a massage is performed on an area adjacent to the vertebrae associated with the disease, an area-by-area pattern in which a massage is performed on vertebrae associated with a certain area of the human body, a sympathetic nerve pattern in which a massage is performed on the sympathetic nerve zone, a parasympathetic nerve pattern in which a massage is performed on the parasympathetic nerve zone, a moxibustion pattern in which moxibustion is performed on moxibustion points associated with the disease, and an acupressure pattern in which acupressure is performed on acupressure points associated with a disease. In this case, the treatment mode is composed of a plurality of patterns obtained by combining the patterns to meet a purpose of treating a disease in the treatment mode.

The fourth operation is to set and store a finishing mode (S404). The finishing mode is a mode for inducing balancing of the autonomic nerves and normalizing a user's condition so that a user can continue with normal life after the massage when the nerves or muscles of the spine are relaxed or excessively strained or the sympathetic nerves are excessively activated during the treatment mode. Thus, depending on in which of the patterns a massage is performed in the treatment mode, the corresponding pattern is properly selected to form a finishing mode. The finishing mode is composed of a parasympathetic nerve pattern in which balancing of the autonomic nerves is induced, a straining pattern in which relaxed muscles are normalized, a relax pattern in which strained nerves are relaxed, and the like.

The fifth operation is to control the motor and the moxibustion device at the controller according to the scanning mode, the standby mode, the treatment mode, and the finishing mode (S405). The patterns constituting the scanning mode, the standby mode, the treatment mode, and the finishing mode are stored in the memory unit, and the controller receives the above-described modes from the memory unit in a sequential order, and controls the moxibustion device and the motor to perform a massage.

Figure 15:
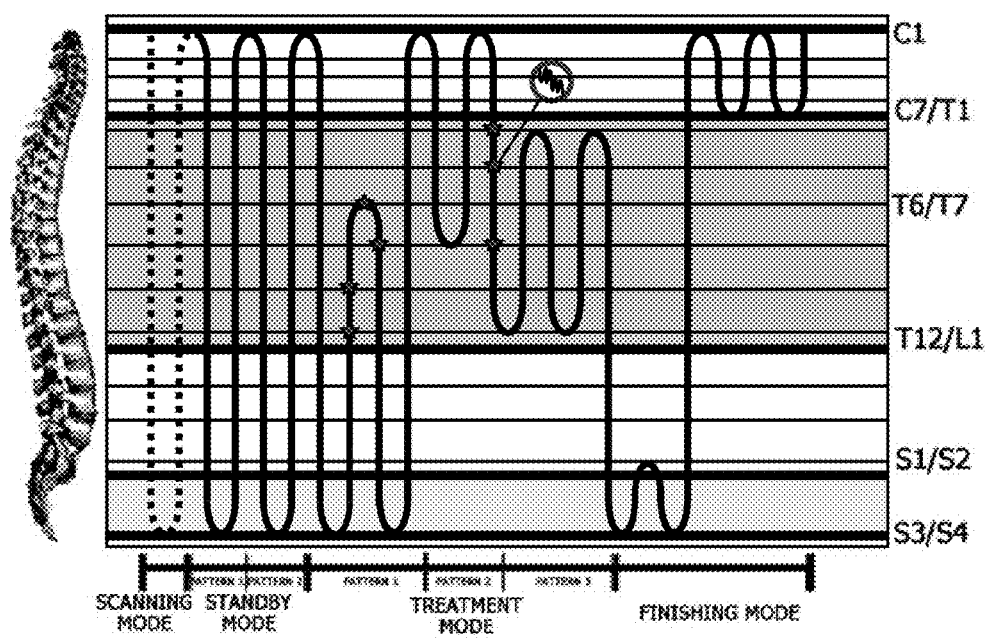
FIG. 15 is a diagram explaining one exemplary embodiment of a massage mode according to the present invention.

FIG. 15 is a diagram showing one exemplary embodiment of a massage mode. Referring to FIG. 15, the scanning mode is composed of a single pattern, and the moxibustion device is driven at a "slow" moving speed, a "strong" massage pressure, and a pattern of one reciprocation. The standby mode is composed of an ease pattern and a strengthening pattern. The ease pattern is set with a "middle" moving speed, a "weak" massage pressure, and a pattern type of one reciprocation, and the strengthening pattern is set with a "middle" moving speed, a "strong" massage pressure, and a pattern type of one reciprocation. The treatment mode is composed of a total of 5 patterns, that is, one area pattern in which a massage is performed on an area adjacent to the vertebrae associated with the disease, one intensive pattern in which a massage is intensively performed on vertebrae associated with a disease, one sympathetic nerve pattern in which a massage is performed on the sympathetic nerve zone, one moxibustion pattern in which moxibustion is performed on moxibustion points associated with a disease, and one acupressure pattern in which acupressure is performed on acupressure points associated with a disease, and thus performs an intensive massage to treat blood circulation disorders. The finishing mode is composed of a total of 2 patterns, that is, one parasympathetic nerve pattern in which the parasympathetic nerves are activated to ease stimuli to the sympathetic nerves in the treatment mode, and one relax pattern in which muscles are relaxed by massaging vertebrae around the neck, and thus the balance of the autonomic nerves is maintained.

The invention claimed is:

1. A method for setting a massage pattern of a thermotherapy device comprising a moxibustion device, a motor, a transfer unit, a controller, an input unit and a memory unit, the method comprising:
    a first operation of driving the moxibustion device to scan the entire spine of a user, setting articulation points between vertebrae of the user as reference points for the human spine composed of cervical vertebrae, thoracic vertebrae, lumbar vertebrae, and a sacrum/coccyx, and storing the articulation points in the memory unit at the controller;
    a second operation of receiving information on related vertebrae associated with dyspepsia, blood circulation, immune boosting, sexual dysfunction, attention deficit disorder, insomnia, obesity, cervical vertebrae pain or lumbar disc, and storing the information in the memory unit at the controller;
    a third operation of receiving information on a moving path on which the moxibustion device actually moves with respect to the reference points while performing a massage on the vertebrae associated with dyspepsia, blood circulation, immune boosting, sexual dysfunction, attention deficit disorder, insomnia, obesity, cervical vertebrae pain or lumbar disc, receiving information on what times the moxibustion device repeatedly performs the massage while moving along the moving path, setting massage patterns according to the dyspepsia, blood circulation, immune boosting, sexual dysfunction, attention deficit disorder, insomnia, obesity, cervical vertebrae pain and lumbar disc, and storing the massage pattern in the memory unit at the controller; and
    a fourth operation of searching for the corresponding massage pattern, receiving the corresponding massage pattern from the memory unit, and controlling the moxibustion device and the motor to perform a massage according to the set massage pattern at the controller when information on the dyspepsia, blood circulation, immune boosting, sexual dysfunction, attention deficit disorder, insomnia, obesity, cervical vertebrae pain or lumbar disc is input through the input unit,
    wherein the reference points are points for establishing landmarks to set the massage pattern, and wherein the reference points become starting points and end points of the massage patterns;
    the massage pattern is different depending on the dyspepsia, blood circulation, immune boosting, sexual dysfunction, attention deficit disorder, insomnia, obesity, cervical vertebrae pain or lumbar disc;
    the massage pattern includes the moving path, a movement repeat count, a moving speed, a massage pressure and a temperature of the moxibustion device;
    the moving path is divided into a plurality of sections, the plurality of sections being adjacent to the vertebrae related with dyspepsia, blood circulation, immune boosting, sexual dysfunction, attention deficit disorder, insomnia, obesity, cervical vertebrae pain or lumbar disc; and
    the movement repeat count, the moving speed, the massage pressure and the temperature of the moxibustion device are differently set for each section of the moving path according to the dyspepsia, blood circulation, immune boosting, sexual dysfunction, attention deficit disorder, insomnia, obesity, cervical vertebrae pain or lumbar disc.

2. The method of claim 1, wherein the second operation comprises:
    operation 2-1 of receiving information on related organs, muscles or body parts according to user's dyspepsia, blood circulation, immune boosting, sexual dysfunction, attention deficit disorder, insomnia, obesity, cervical vertebrae pain or lumbar disc;
    operation 2-2 of receiving information on vertebrae corresponding to the organs, the muscles or the body parts when the organs, the muscle or the body parts are determined.

3. The method of claim 1, wherein the massage pattern is repeated more than once for the dyspepsia, blood circulation, immune boosting, sexual dysfunction, attention deficit disorder, insomnia, obesity, cervical vertebrae pain or lumbar disc.

4. The method of claim 3, wherein the controller transfers a signal value to the motor to control a massage moving path, a repeat count, a moving speed and a massage pressure in the massage pattern, and transfers the signal value to the moxibustion device to control a temperature of the moxibustion device.

5. A thermotherapy device comprising:
    a moxibustion device 110 configured to move in a longitudinal direction of the spine of a user;
    a transfer unit 126 coupled to the motor 140 and configured to provide a turning force of the motor 140 to translocate the moxibustion device;
    an input unit configured to receive a user's operation signal and provide the operation signal to the controller;
    a memory unit configured to store information on a massage pattern according to dyspepsia, blood circulation, immune boosting, sexual dysfunction, attention deficit disorder, insomnia, obesity, cervical vertebrae pain or lumbar disc including a moving path of the moxibustion device, a massage count, a moving speed of the moxibustion device, a massage pressure, and a temperature of the moxibustion device;
    a controller configured to search for the corresponding massage pattern, receive the corresponding massage pattern from the memory unit, and control the moxibustion device and the motor to perform a massage according to the set massage pattern when information on the dyspepsia, blood circulation, immune boosting, sexual dysfunction, attention deficit disorder, insomnia, obesity, cervical vertebrae pain or lumbar disc is input through the input unit,
    wherein information on reference points of the user spine and related vertebrae associated with dyspepsia, blood circulation, immune boosting, sexual dysfunction, attention deficit disorder, insomnia, obesity, cervical vertebrae pain or lumbar disc is further included in the memory unit, wherein the information on the reference points comprises articulation points between the vertebrae of the user set as the reference points by causing the controller to drive the moxibustion device to scan the entire spine of a user, wherein the reference points are points for establishing landmarks to set the massage pattern, wherein the reference points become starting points and end points of the massage patterns;
    the massage pattern is different depending on the dyspepsia, blood circulation, immune boosting, sexual dysfunction, attention deficit disorder, insomnia, obesity, cervical vertebrae pain or lumbar disc;

the massage pattern includes the moving path, a movement repeat count, a moving speed, a massage pressure and a temperature of the moxibustion device;

the moving path is divided into a plurality of sections, the plurality of sections being adjacent to the vertebrae related with dyspepsia, blood circulation, immune boosting, sexual dysfunction, attention deficit disorder, insomnia, obesity, cervical vertebrae pain or lumbar disc; and the movement repeat count, the moving speed, the massage pressure and the temperature of the moxibustion device are differently set for each section of the moving path according to the dyspepsia, blood circulation, immune boosting, sexual dysfunction, attention deficit disorder, insomnia, obesity, cervical vertebrae pain or lumbar disc.

6. The thermotherapy device of claim 5, wherein the controller stores set information on a moving path of the moxibustion device, a movement repeat count, a moving speed, massage pressure, and a temperature of moxibustion device in the memory unit.

7. A method for setting a massage pattern of a thermotherapy device comprising a moxibustion device, a motor, a transfer unit, a controller, an input unit, and a memory unit, the method comprising:

a first operation of driving the moxibustion device to scan the entire spine of a user, setting articulation points between vertebrae of the user as reference points for the human spine composed of cervical vertebrae, thoracic vertebrae, lumbar vertebrae, and a sacrum/coccyx, and storing the articulation points in the memory unit at the controller;

a second operation of dividing an autonomic nerve zone of the spine into a sympathetic nerve zone and a parasympathetic nerve zone with respect to the reference points according to distribution of the peripheral nerves of the spine, and storing the sympathetic nerve zone and the parasympathetic nerve zone in the memory unit at the controller;

a third operation of receiving information on a relationship between dyspepsia, blood circulation, immune boosting, sexual dysfunction, attention deficit disorder, insomnia, obesity, cervical vertebrae pain or lumbar disc and sympathetic and parasympathetic nerves, and storing the information in the memory unit at the controller;

a fourth operation of receiving information on a moving path on which the moxibustion device actually moves while performing a massage on the sympathetic nerve zone and/or the parasympathetic nerve zone in the case of dyspepsia, blood circulation, immune boosting, sexual dysfunction, attention deficit disorder, insomnia, obesity, cervical vertebrae pain or lumbar disc showing a relationship between the sympathetic nerves and the parasympathetic nerves, receiving information on what times the moxibustion device repeatedly performs the massage while moving along the moving path to set a massage pattern according to the dyspepsia, blood circulation, immune boosting, sexual dysfunction, attention deficit disorder, insomnia, obesity, cervical vertebrae pain or lumbar disc, and storing the massage pattern at the controller; and a fifth operation of searching for a massage pattern, receiving the massage pattern from the memory unit, and controlling the moxibustion device and the motor to perform a massage according to the set massage pattern at the controller when information on the dyspepsia, blood circulation, immune boosting, sexual dysfunction, attention deficit disorder, insomnia, obesity, cervical vertebrae pain or lumbar disc showing the relationship between the sympathetic nerves and the parasympathetic nerves is input through the input unit, wherein the reference points are points for establishing landmarks to set the massage pattern, wherein the reference points become starting points and end points of the massage patterns;

the massage pattern is different depending on the dyspepsia, blood circulation, immune boosting, sexual dysfunction, attention deficit disorder, insomnia, obesity, cervical vertebrae pain or lumbar disc;

the massage pattern includes the moving path, a movement repeat count, a moving speed, a massage pressure and a temperature of the moxibustion device;

the moving path is divided into a plurality of sections, the plurality of sections being adjacent to the vertebrae related with dyspepsia, blood circulation, immune boosting, sexual dysfunction, attention deficit disorder, insomnia, obesity, cervical vertebrae pain or lumbar disc; and the movement repeat count, the moving speed, the massage pressure and the temperature of the moxibustion device are differently set for each section of the moving path according to the dyspepsia, blood circulation, immune boosting, sexual dysfunction, attention deficit disorder, insomnia, obesity, cervical vertebrae pain or lumbar disc.

8. The method of claim 7, wherein the massage pattern comprises a moving speed of the moxibustion device, a massage pressure, and a temperature of the moxibustion device in the third operation.

9. The method of claim 8, wherein the massage is performed on the sympathetic nerves followed by the parasympathetic nerves when the massage has to be performed on both of the sympathetic nerve zone and the parasympathetic nerve zone.

10. The method of claim 7, wherein the massage pattern comprises the massage order determining which of the sympathetic nerve zone and the parasympathetic nerve zone is massaged first in the third operation when the sympathetic nerve zone and the parasympathetic nerve zone have to be massaged.

11. The method of claim 7, wherein the massage pressure applied to the sympathetic nerves is stronger than that applied to the parasympathetic nerves.

12. A method for setting a massage pattern of a thermotherapy device comprising a moxibustion device, a motor, a transfer unit, a controller, an input unit, and a memory unit, the method comprising:

a first operation of driving the moxibustion device to scan the entire spine of a user, setting articulation points between vertebrae of the user as reference points for the human spine composed of cervical vertebrae, thoracic vertebrae, lumbar vertebrae, and a sacrum/coccyx, and storing the articulation points in the memory unit at the controller;

a second operation of receiving information on positions of related moxibustion points and acupressure points associated with dyspepsia, blood circulation, immune boosting, sexual dysfunction, attention deficit disorder, insomnia, obesity, cervical vertebrae pain or lumbar disc, and storing the information in the memory unit at the controller;

a third operation of receiving information on a moxibustion intensity, a moxibustion temperature, and a moxibustion time for the moxibustion points, setting a moxibustion pattern, and storing the moxibustion pattern in the memory unit at the controller;

a fourth operation of receiving information on an acupressure intensity, an acupressure time, and an acupressure operation for the acupressure points, setting an acupressure pattern, and storing the acupressure pattern in the memory unit at the controller; and a fifth operation of searching for a corresponding moxibustion pattern and a corresponding acupressure pattern, receiving the corresponding moxibustion pattern and corresponding acupressure pattern from the memory unit, and controlling the moxibustion device and the motor to perform moxibustion and acupressure according to the corresponding moxibustion pattern and the corresponding acupressure pattern at the controller when the moxibustion device reaches the reference points at which predetermined moxibustion points and acupressure points are positioned as the moxibustion device is performing a massage according to a set massage pattern according to the dyspepsia, blood circulation, immune boosting, sexual dysfunction, attention deficit disorder, insomnia, obesity, cervical vertebrae pain or lumbar disc when dyspepsia, blood circulation, immune boosting, sexual dysfunction, attention deficit disorder, insomnia, obesity, cervical vertebrae pain or lumbar disc is selected through the input unit, wherein the reference points are points for establishing landmarks to set the massage pattern, wherein the reference points become starting points and end points of the massage patterns;

the massage pattern is different depending on the dyspepsia, blood circulation, immune boosting, sexual dysfunction, attention deficit disorder, insomnia, obesity, cervical vertebrae pain or lumbar disc;

the massage pattern includes the moving path, a movement repeat count, a moving speed, a massage pressure and a temperature of the moxibustion device;

the moving path is divided into a plurality of sections, the plurality of sections being adjacent to the vertebrae related with dyspepsia, blood circulation, immune boosting, sexual dysfunction, attention deficit disorder, insomnia, obesity, cervical vertebrae pain or lumbar disc; and the movement repeat count, the moving speed, the massage pressure and the temperature of the moxibustion device are differently set for each section of the moving path according to the dyspepsia, blood circulation, immune boosting, sexual dysfunction, attention deficit disorder, insomnia, obesity, cervical vertebrae pain or lumbar disc.

13. The method of claim 12, wherein the moxibustion points and the acupressure points in the second operation are positioned at the reference points.

14. The method of claim 13, wherein the acupressure operation in the fourth operation is divided into a horizontal vibration, a vertical vibration, a rotation, and a combination thereof.

15. A method for setting a massage mode of a thermotherapy device comprising a moxibustion device, a motor, a moving unit, a controller, an input unit, and a memory unit, the method comprising:

a first operation of performing a scanning mode which is performed by driving the moxibustion device to scan the entire spine of a user, setting articulation points between vertebrae of the user as reference points for the human spine composed of cervical vertebrae, thoracic vertebrae, lumbar vertebrae, and a sacrum/coccyx, and storing the articulation points in the memory unit at the controller;

a second operation of receiving patterns in which tension applied to all spinal nerves or muscles is eased so that the spine sufficiently endures massage stimuli without any pain, combining the patterns to set a standby mode, and storing the standby mode in the memory unit at the controller;

a third operation of receiving predetermined patterns based on vertebrae, moxibustion points and acupressure points, all of which are associated with dyspepsia, blood circulation, immune boosting, sexual dysfunction, attention deficit disorder, insomnia, obesity, cervical vertebrae pain or lumbar disc, in order to treat the dyspepsia, blood circulation, immune boosting, sexual dysfunction, attention deficit disorder, insomnia, obesity, cervical vertebrae pain or lumbar disc, combining the patterns to set a treatment mode, and storing the treatment mode in the memory unit at the controller;

a fourth operation of receiving patterns for inducing balancing of autonomic nerves and normalizing a user's condition, combining the patterns to set a finishing mode, and storing the finishing mode in the memory unit at the controller; and a fifth operation of controlling the motor and the moxibustion device in a sequential order at the controller according to the scanning mode, the standby mode, the treatment mode, and the finishing mode when information on dyspepsia, blood circulation, immune boosting, sexual dysfunction, attention deficit disorder, insomnia, obesity, cervical vertebrae pain or lumbar disc is input through the input unit, wherein the controller is controlling the moxibustion device to perform a massage according to a set massage pattern, wherein the reference points are points for establishing landmarks to set the massage pattern, wherein the reference points become starting points and end points of the massage patterns;

the massage pattern is different depending on the dyspepsia, blood circulation, immune boosting, sexual dysfunction, attention deficit disorder, insomnia, obesity, cervical vertebrae pain or lumbar disc;

the massage pattern includes the moving path, a movement repeat count, a moving speed, a massage pressure and a temperature of the moxibustion device;

the moving path is divided into a plurality of sections, the plurality of sections being adjacent to the vertebrae related with dyspepsia, blood circulation, immune boosting, sexual dysfunction, attention deficit disorder, insomnia, obesity, cervical vertebrae pain or lumbar disc; and the movement repeat count, the moving speed, the massage pressure and the temperature of the moxibustion device are differently set for each section of the moving path according to the dyspepsia, blood circulation, immune boosting, sexual dysfunction, attention deficit disorder, insomnia, obesity, cervical vertebrae pain or lumbar disc.

16. The method of claim 15, wherein the scanning mode in the first operation is set with a "slow" moving speed, and a single pattern of one reciprocation.

17. The method of claim 15, wherein the treatment mode in the third operation is configured to select a plurality of patterns from an intensive pattern in which a massage is intensively performed on vertebrae associated with a disease, a whole pattern in which a massage is performed on the entire spine, an area pattern in which a massage is performed on an area adjacent to the vertebrae associated with the disease, an area-by-area pattern in which a massage is performed on vertebrae associated with a certain area of the human body, a sympathetic nerve pattern in which a massage is performed on the sympathetic nerve zone, a parasympathetic nerve pattern in which a massage is performed on the parasympathetic nerve zone, a moxibustion pattern in which moxibustion is performed on moxibustion points associated with the disease, and an acupressure pattern in which acupressure is performed on acupressure points associated with a disease.

18. The method of claim 15, wherein the finishing mode in the fourth operation is configured to select a pattern from a parasympathetic nerve pattern in which balancing of the autonomic nerves is induced, a straining pattern in which relaxed muscles are normalized, and a relax pattern in which strained nerves are relaxed.

* * * * *